United States Patent
Huang et al.

(10) Patent No.: US 7,527,964 B2
(45) Date of Patent: *May 5, 2009

(54) METHOD FOR CLEAVAGE OF ETHER-LINKAGES IN POLYETHOXYLATES

(75) Inventors: Shir-Ly Huang, Jungli (TW); Gia-Luen Guo, Jungli (TW)

(73) Assignee: National Central University, Taoyuan (TW)

( * ) Notice: Subject to any disclaimer, the term of this patent is extended or adjusted under 35 U.S.C. 154(b) by 683 days.

This patent is subject to a terminal disclaimer.

(21) Appl. No.: 10/874,619

(22) Filed: Jun. 22, 2004

(65) Prior Publication Data

US 2005/0075515 A1 Apr. 7, 2005

(30) Foreign Application Priority Data

Oct. 6, 2003 (TW) .............................. 92127635 A

(51) Int. Cl.
- *B09B 3/00* (2006.01)
- *C02F 3/34* (2006.01)
- *C12N 1/20* (2006.01)

(52) U.S. Cl. ................. 435/262; 435/253.3; 435/262.5; 435/874

(58) Field of Classification Search ....................... None
See application file for complete search history.

(56) References Cited

U.S. PATENT DOCUMENTS 7,115,411 B2 * 10/2006 Huang ...................... 435/253.3
7,332,325 B2 * 2/2008 Huang et al. ............. 435/262.5

OTHER PUBLICATIONS

Tanghe et al, Applied and Env. Microb., Feb. 1999, vol. 65, No. 2, pp. 746-751.*
Iizuka et al, J. of Gen. App. Microb., 1964, vol. 10, No. 3, pp. 207-221.*
Maki et al, App. and Env. Microb., Jul. 1994, vol. 60, No. 7, pp. 2265-2271.*
Sato et al, Polymer Degrad. and Stability, 2001, vol. 74, pp. 69-75.*

* cited by examiner

Primary Examiner—David M. Naff
Assistant Examiner—Deborah K. Ware
(74) Attorney, Agent, or Firm—J.C. Patents

(57) ABSTRACT

A method for cleavage of the ether-linkage of polyethoxylates is described. A novel pure microbial culture, *Pseudomonas nitroreducens* TX1 (Depository No.: BCRC910228), is used under aerobic condition to cleave the ether-linkage adjacent to the carboxylated terminus or ethoxyl terminus. This method is useful to cleave sequentially ether-linkage of polyethoxylates in an aqueous buffer solution with an initial concentration of the polyethoxylates between 0.05% and 20%. This method is also effective for the cleavage of the ether-linkages in short-chain polyethoxylates with one to three ethoxyl units.

7 Claims, 3 Drawing Sheets

METHOD FOR CLEAVAGE OF ETHER-LINKAGES IN POLYETHOXYLATES

CROSS-REFERENCE TO RELATED APPLICATION

This application claims the priority benefit of Taiwan application serial no. 92127635, filed on Oct. 6, 2003.

BACKGROUND OF THE INVENTION

1. Field of the Invention

The present invention generally relates to a method of bio-catalysis and, more particularly, to a method of bio-catalysis for the cleavage of ether-linkages in polyethoxylates.

2. Description of the Related Art

Polymers have been widely used in industrial, agricultural and other socioeconomic activities. Polymers, more particularly alkylphenol polyethoxylates, are used as surfactants. However, once the surfactants containing alkylphenol polyethoxylates are discharged into the environment, metabolites from the surfactants tend to be accumulated in soil or water, and may have an environmental hormone effect that causes damage to ecological systems and human health. As a result, the environmental problems related to alkylphenol polyethoxylates have drawn public attention worldwide. In addition, during the bioremediation processes of petrochemical pollutants in soil and groundwater, surfactants are often used as additives to facilitate the degradation of petroleum compounds, and thus there is a need to remove these surfactants to protect the environment from secondary pollution.

Currently, chemical oxidation technologies are usually used to deal with such polyethoxylate related environmental pollution problems. In other words, conventional chemical oxidation methods are often used to degrade the polyethoxylates to solve pollution problems caused by organo-polymers.

However, the chemical oxidation methods require the use of large amount of energy, and may cause other forms of pollution in the environment. Therefore, the use of a bio-catalytic process would be highly useful as a means of degrading organo-polymers for environmental protection and biological restoration.

SUMMARY OF THE INVENTION

The object of the present invention is to provide a bio-catalytic process for the degradation of polyethoxylates by cleavage of the ether-linkage thereof.

Therefore, in accordance with the above objective and other advantages of the present invention, as broadly embodied and described herein, the present invention provides a method of cleaving the ether-linkage of polyethoxylates. Specifically, a novel, isolated pure microbial culture *Pseudomonas nitroreducens* TX1 (BCRC910228) is used under aerobic condition to convert the ethoxyl terminus of polyethoxylates into a carboxylated terminus, and then it cleaves the ether-linkage adjacent to the carboxylated terminus. The microbial culture is a Gram-negative rod-shaped bacterium. This novel pure microbial culture is able to cleave sequentially the ether-linkages of polyethoxylates in an aqueous buffer solution with an initial concentration of the polyethoxylates above 0.05% or between 0.05% and 20%, and is also effective at cleaving ether-linkages of short-chain polyetoxylates with one to three ethoxyl units. The short-chain polyethoxylates have been shown to have estrogen-like activity.

In contrast to conventional chemical oxidation methods, the biological method of the present invention, which utilizes a novel pure microbial culture to cleave ether-linkages in order to degrade organo-polymers, uses less energy and is more environmentally friendly.

It is to be understood that both the foregoing general description and the following detailed description are exemplary, and are intended to provide further explanation of the invention as claimed.

A deposit of the biological material has been made on Aug. 26, 2004 at ATCC (American Type Culture Collection), 10801 University Blvd., Manassas, Va. 20110-2209, USA with an accession number PTA-6168. The biological material is a Gram-negative, rod shaped bacterium *Pseudomonas nitroreducens* TX1.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
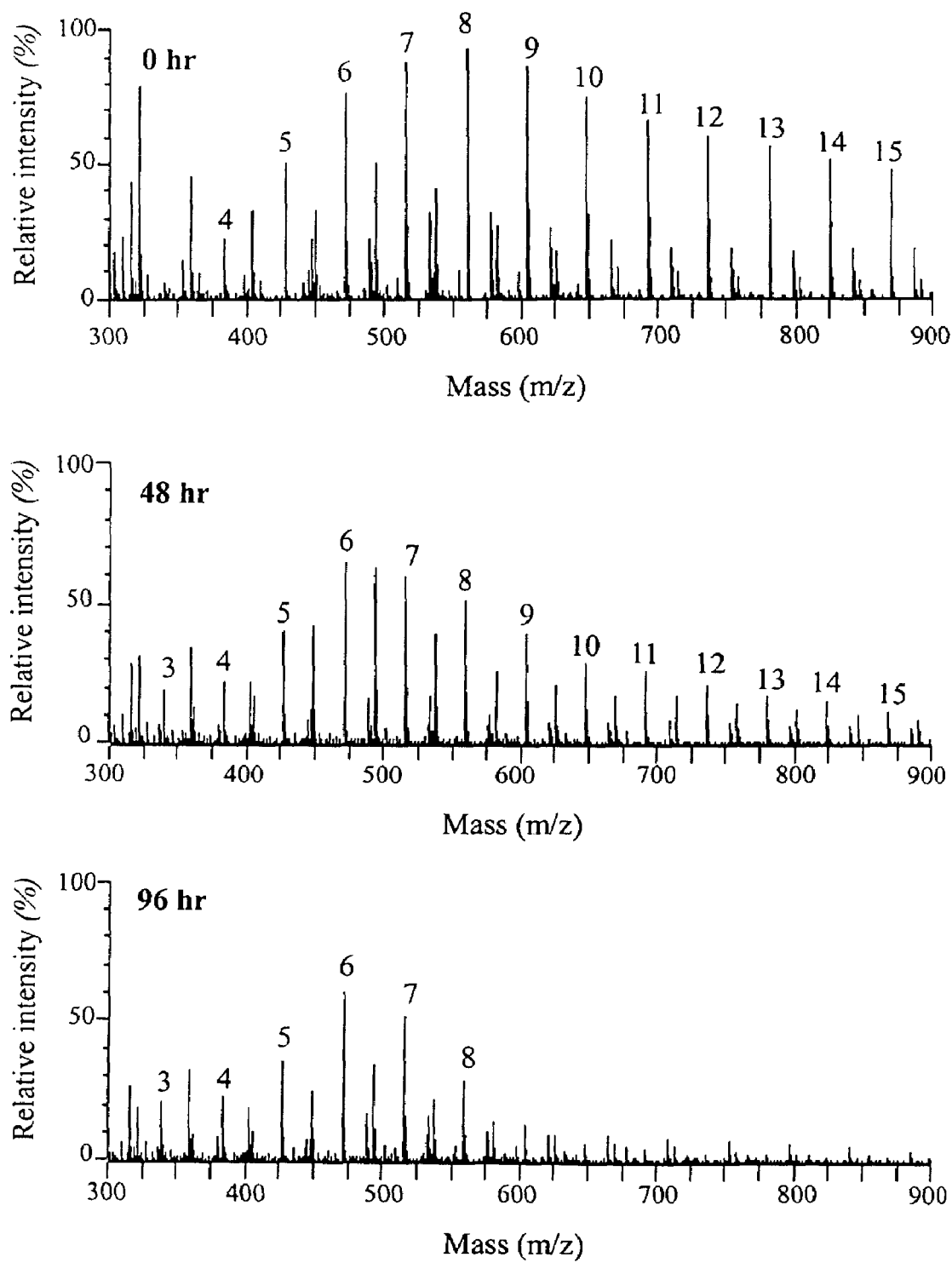
FIG. 1 is liquid chromatography-mass spectra showing the products of octylphenol polyethoxylates degraded by the novel pure culture in accordance with one embodiment of the present invention.

The following is a description of the preferred embodiments of the present invention, as illustrated in the accompanying figures (FIGS. 1, 2 and 3) and are set forth for the purpose of explanation and not limitation, to provide a thorough understanding of the present invention.

The present invention provides a method of using a microbial culture to cleave ether-linkages in order to degrade polymers. The culture (*Pseudomonas nitroreducens* TX1) that is used in the present invention was deposited on Aug. 6, 2003, at Biological Resources Depository and Research Center (BRDRC) at Institute of Food Industrial Research and Development, R.O.C. The depository number of the culture is BCRC910228. The microbial culture is a Gram-negative rod-shaped bacterium *Pseudomonas nitroreducens* TX1. The characteristics and relevant information of the pure novel culture of *Pseudomonas nitroreducens* TX1 are disclosed in R.O.C. Patent Application 92126305.

In the present invention, a pure culture of *Pseudomonas nitroreducens* TX1 is used under aerobic condition, especially between pH6 and pH8, to convert the ethoxyl terminus of the polyethoxylates into a carboxylated terminus and then to cleave the ether-linkage next to a carboxylated terminus. The compounds containing polyethoxylates can be alkylphenol polyethoxylates, dodecyl octaethoxylates, polyethylene glycol, 1,4-dioxane, trioxane, and cyclic ether. In one preferred embodiment, the polyethoxylates are, for example, polyethoxylates having one to 20 ethoxyl units. An example of such polyethoxylates is akylphenol polyethoxylates with 1 to 20 ethoxyl units ($OCH_2CH_2$) and an alkyl chain (R: $C_mH_{2m+1}$, $m \geq 1$), which has the formula (1):

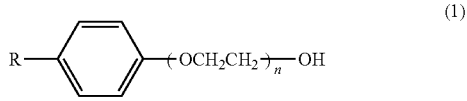

(1)

It should be noted that the culture of *Pseudomonas nitroreducens* TX1 used in the present invention is effective at cleaving the ether-linkage of polyethoxylates in an aqueous buffer solution with a broad initial concentration of the polyethoxylates from 0.05% to 20%. In addition, the cleavage is selective such that the ether-linkage of the polyethoxylates is cleaved sequentially. It should also be noted that the method of the present invention is capable of cleaving ether-linkages of polyethoxylates with different numbers of ethoxyl units, and is also effective at cleavage of ether-linkages of short-chain polyethoxylates having one to three ethoxyl units.

The present invention is further described in another preferred embodiment, where octylphenol polyethoxylates (OPEOn) are used, to illustrate the cleavage mechanism. The ethoxyl unit of octylphenol polyethoxylates is shortened through the cleavage of ether-linkage adjacent to the carboxylated terminus or ethoxyl terminus. Moreover, the ethoxyl terminus of the octylphenol polyethoxylates is carboxylated before or after the cleavage of ether-linkage, as shown in the following reaction scheme (2):

chain octylphenol polyethoxylates after four hours of degradation process, where n ranges from 1 to 3 and refers to the number of ethoxyl units of the products. The liquid chromatography was performed using a mobile phase in gradient with the ratio of acetonitrile changing from 30% to 90% over 40 minutes. In addition, the mass spectrometry was performed with a corn potential of 25 V.

Figure 3:
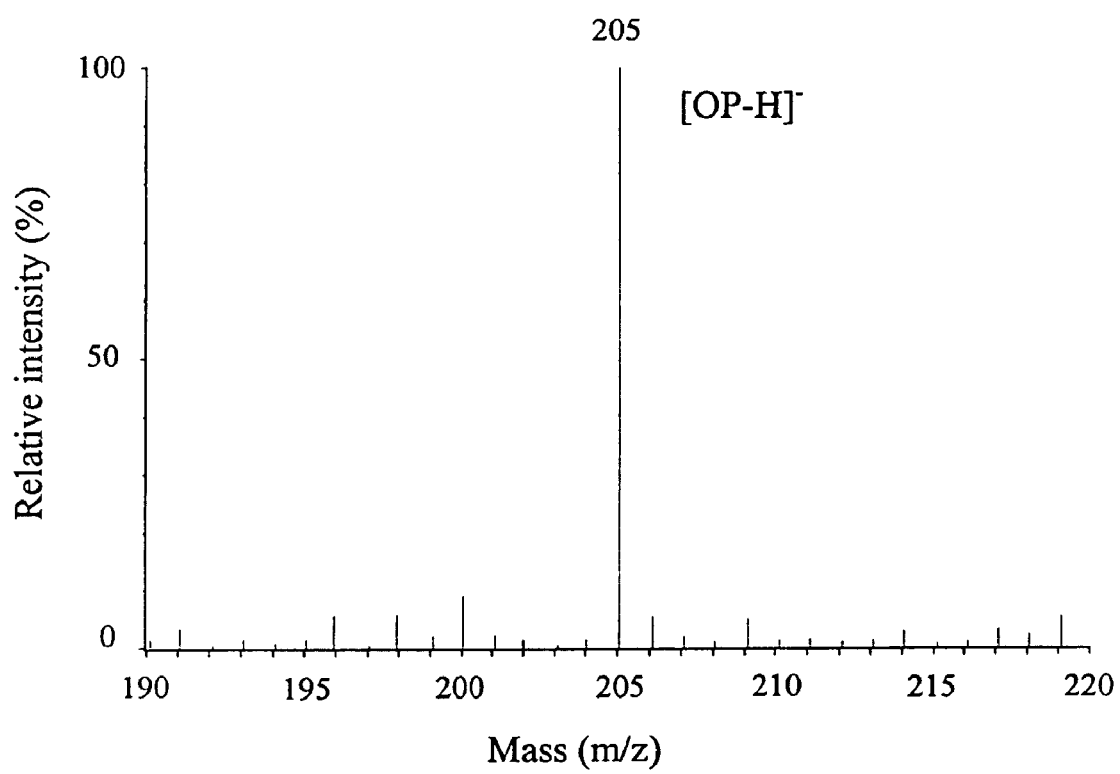
FIG. 3 is a mass spectrum showing octylphenol as a product from octylphenol polyethoxylates after four hours of degradation process.

FIG. 3 is a mass spectrum showing octylphenol (OP) as a product from octylphenol polyethoxylates after four hours of degradation process. The liquid chromatography was performed by using a mobile phase with 90% of acetonitrile. In addition, the mass spectrometry was performed by using an electron spray ionization mass spectrometer in a negative mode, where the capillary potential was 3.0 V and the corn potential was 50 V.

Referring to FIG. 1, the culture of *Pseudomonas nitroreducens* TX1 is used to cleave sequentially the ether-linkage of octylphenol polyethoxylates, and hence the chain of the octylphenol polyethoxylates becomes shorter gradually. Further referring to FIGS. 2 and 3, after 4 hours of degradation of octylphenol polyethoxylates, the spectra of the degradation products indicate the existence of both octylphenol and carboxylated short-chain octylphenol polyethoxylates with one to three ethoxyl units. Therefore, the foregoing results indicate that the culture capable of generating carboxylated

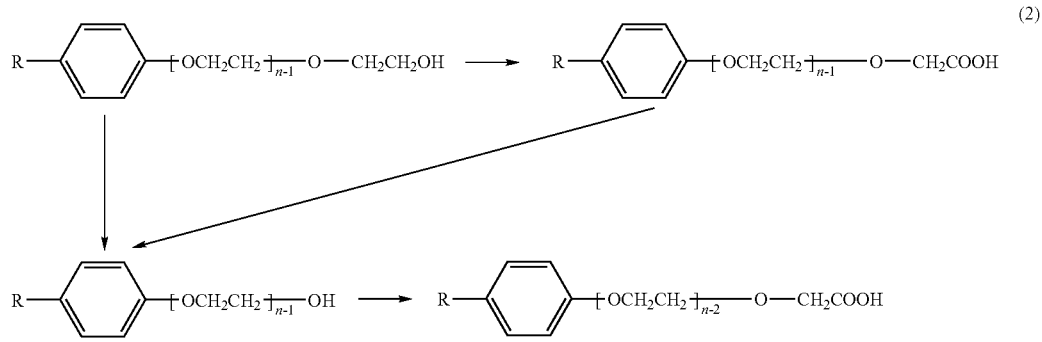

(2)

As shown in the foregoing scheme, by using a culture of *Pseudomonas nitroreducens* TX1 as part of the present invention, the ethoxyl terminus of the octylphenol polyethoxylates is carboxylated before or after the cleavage of ether-linkage. As the process of carboxylation and cleavage is repeated, the ethoxyl chain of the octylphenol polyethoxylates becomes shorter.

FIG. 1 shows the liquid chromatograph-mass spectra identifying the products from octylphenol polyethoxylates degraded by the culture of *Pseudomonas nitroreducens* TX1 over a time period ranging over 0, 48 and 96 hours. Liquid chromatography was performed using a high pressure liquid chromatograph (Water Alliance 2690) and C18 column (μ Bondapak, 3.9×150 mm) with acetonitrile and 0.1% aqueous formic acid (1:1) as the mobile phase. Further, the mass spectrometry was performed by using an electron spray ionization mass spectrometer (Platform LC, Micromass) in a positive mode, where the capillary potential was 3.5 V, the corn potential was 35 V, the inlet temperature was 100° C., and the nitrogen flow rate was 300 l/h.

Figure 2:
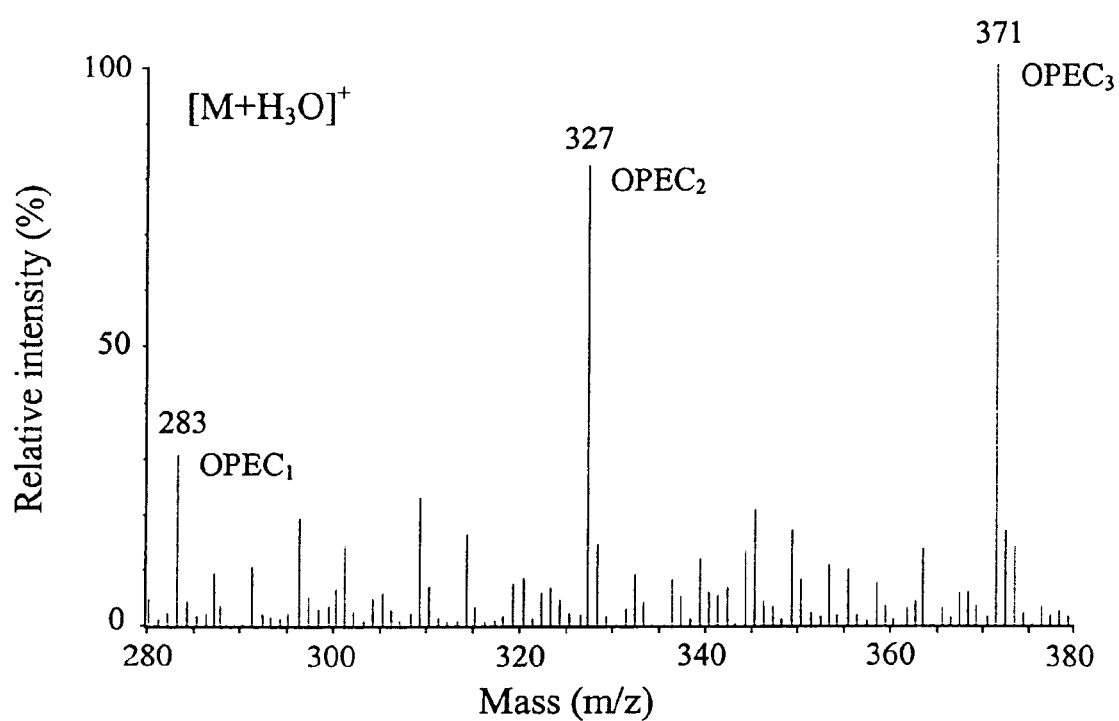
FIG. 2 is a mass spectrum showing octylphenol polyethoxyl carboxylates (OPECn) as the products from short-chain octylphenol polyethoxylates after four hours of degradation process.

FIG. 2 is a mass spectrum showing octylphenol polyethoxyl carboxylates (OPECn) as the products from shortoctylphenol polyethoxylates having one to three ethoxyl units, and octylphenol is also formed after the ether-linkage is fully cleaved.

The foregoing results show that the present invention discloses a mechanism wherein the ethoxyl terminal of the polyethoxylates is carboxylated before or after the cleavage of the ether-linkage. The chain of the polyethoxylates becomes shorter sequentially through the cleavage of ether-linkage adjacent to carboxylated terminus or ethoxyl terminus.

The present invention provides a process that is capable of cleaving ether-linkage of polyethoxylates having different numbers of ethoxyl units, and, is also effective at cleavage of the ether-linkage of short-chain polyethoxylates with one to three ethoxyl units. This property has not yet been disclosed by any conventional technology, which employs a pure microbial culture for the cleavage of ether-linkages; that is, no previously identified microbial culture is known to be able to cleave the ether-linkage of short-chain polyethoxylates. The prior art references, incorporated herein by reference, include: Hideaki M., N. Masuda, Y. Fujiwara, M. Ika, and M. Fujika, Appl. Environ. Microbiol., 60: 2265-71 (1994); Dominic M. J., and G. F. White, *J. Bacteriol.*, 180: 4332-38

(1998); Nguyen M. H. and J. C. Sigoillot, *Biodegradation*, 7: 369-75 (1997); Sato H., A. Shibata, Y. Wang, H. Yoshikawa, and H. Tamura, *Polymer Degradation and Stability*, 74: 69-75 (2001); Nishio E., Y. Ichiki, H. Tamura, and S. Morita, *Biosci. Biotechnol. Biochem.*, 66: 1792-98 (2002); or Sato H., A. Shibata, Y Wang, H. Yoshikawa, and H. Tamura, *Biomacromolecules*, 4: 46-51 (2003).

In another preferred embodiment of the present invention, a culture *Pseudomonas nitroreducens* TX1 is placed in a medium containing alkylphenol polyethoxylates, and 50~90% of the alkylphenol polyethoxylate is degraded within 96 hours via cleavage of the ether-linkage. The above medium is, for example, MSB (mineral salts basal medium). The relevant conditions of MSB has been disclosed in the following publication, which is incorporated herein by reference: R. Y. G. Stanier, C. Bazire, and W. R. Sistrom, Kinetics Studies of Pigment Synthesis by Non-sulfur Purple Bacteria, *J. Cell Comp. Physiol.*, 49: 25-28 (1966).

Since the present invention employs a biological process to cleave ether-linkage of organo-polymers for polymer removal or biological conversion, the method of the present invention is advantageous over the conventional chemical methods as it has a lower energy consumption and a higher environmental compatibility.

In addition, since the present invention results in the ether-linkage of the polyethoxylates being cleaved sequentially, the biological reaction is selective.

Furthermore, the method of the present invention is capable of cleaving ether-linkage of polyethoxylates having different numbers of ethoxyl units, and, is also effective at the cleavage of the ether-linkage of short-chain polyethoxylates with one to three ethoxyl units. No published reports have described such a pure culture that can be used to cleave the ether-linkages of short-chain polyethoxylates.

It will be apparent to those skilled in the art that various modifications and variations can be made to the structure of the present invention without departing from the scope or spirit of the invention. In view of the foregoing, it is intended that the present invention covers modifications and variations of this invention provided, which fall within the scope of the following claims and their equivalents.

What is claimed is:

1. A method for cleaving ether-linkages of polyethoxylates, wherein a biologically pure microbial culture, *Pseudomonas nitroreducens* strain PTA-6168, is used to cleave sequentially the ether-linkages of the polyethoxylates.

2. The method as recited in claim 1, wherein the culture is used to cleave the ether-linkages under aerobic conditions and at pH of 6 to 8.

3. The method as recited in claim 1, wherein the culture is used to cleave the ether-linkages in an aqueous solution above a concentration of 0.05% of the polyethoxylates.

4. The method as recited in claim 1, further comprising carboxylation of ethoxyl terminus of the polyethoxylates.

5. The method as recited in claim 1, wherein number of ethoxyl units on each of the polyethoxylates ranges from 1 to 20.

6. The method as recited in claim 1, wherein the culture is used in a medium containing alkylphenol polyethoxylates to cleave the ether-linkages and degrade more than 90% of the alkylphenol polyethoxylates within 96 hours.

7. The method as recited in claim 1, wherein the polyethoxylates are alkylphenol polyethoxylates, dodecyl octaethoxylates, polyethylene glycol, 1,4-dioxane, trioxane, cyclic ether, or any mixture thereof.

* * * * *